(12) United States Patent
Andersen et al.

(10) Patent No.: US 8,641,990 B2
(45) Date of Patent: Feb. 4, 2014

(54) STORAGE VESSEL AND A BREAK TOOL FOR DIVIDING SUCH VESSEL

(76) Inventors: Ove Andersen, Hellerup (DK); Birgitte Rønde Hansen, Brønshøj (DK); Janne Petersen, København V (DK)

(*) Notice: Subject to any disclaimer, the term of this patent is extended or adjusted under 35 U.S.C. 154(b) by 475 days.

(21) Appl. No.: 12/811,165

(22) PCT Filed: Dec. 30, 2008

(86) PCT No.: PCT/DK2008/050338
§ 371 (c)(1),
(2), (4) Date: Oct. 18, 2010

(87) PCT Pub. No.: WO2009/086829
PCT Pub. Date: Jul. 16, 2009

(65) Prior Publication Data
US 2010/0303688 A1 Dec. 2, 2010

(30) Foreign Application Priority Data
Jan. 7, 2008 (DK) .................... 2008 00021

(51) Int. Cl.
*B01L 3/14* (2006.01)
*B01L 3/00* (2006.01)
*B01L 9/00* (2006.01)
*B01L 9/06* (2006.01)

(52) U.S. Cl.
USPC ............ 422/549; 422/559; 422/561; 422/562

(58) Field of Classification Search
USPC ........................................... 422/549
See application file for complete search history.

(56) References Cited

U.S. PATENT DOCUMENTS

| | | | | |
|---|---|---|---|---|
| 1,718,599 A * | 6/1929 | Smith | ............ | 604/234 |
| 2,335,799 A * | 11/1943 | Schwab | ............ | 604/148 |
| 2,383,089 A * | 8/1945 | Theiler | ............ | 285/55 |
| 2,447,988 A * | 8/1948 | Pierson | ............ | 451/557 |
| 2,693,183 A * | 11/1954 | Lockhart | ............ | 604/201 |
| 3,297,184 A * | 1/1967 | Andelin | ............ | 215/307 |
| 4,353,869 A * | 10/1982 | Guth | ............ | 422/558 |
| 5,278,941 A * | 1/1994 | Ward | ............ | 392/498 |
| 5,645,715 A * | 7/1997 | Coombs | ............ | 210/94 |
| 5,916,527 A | 6/1999 | Haswell | | |
| 6,383,453 B1 * | 5/2002 | Banauch et al. | ............ | 422/550 |

FOREIGN PATENT DOCUMENTS

| | | |
|---|---|---|
| DE | 197 20 930 | 11/1997 |
| DE | 102 62 157 | 11/2006 |
| GB | 2 072 130 | 9/1981 |
| WO | 87/07501 | 12/1987 |
| WO | 8707571 | 12/1987 |
| WO | 9204978 | 4/1992 |
| WO | 0228733 | 4/2002 |
| WO | 2004042341 | 5/2004 |

* cited by examiner

*Primary Examiner* — Jill Warden
*Assistant Examiner* — Brittany Fisher
(74) *Attorney, Agent, or Firm* — Kristina Bieker-Brady; Clark & Elbing LLP (57) ABSTRACT

The present invention concerns a breakable multi-specimen storage vessel. The vessel comprises a tubular container comprising a lower end and an upper end. At least said upper end has an open end opening. The length of said container is continuously formed and provided with break portions at predetermined positions alongside thereof. Said container is adapted to be broken into a plurality of specimens. Further, an external surface of said container may be provided with a screw thread. Said screw thread is provided extending longitudinally along substantially the entire length of said tubular container and said internal surface is substantially smooth. The invention further relates to a break tool for breaking off specimens from a multi-specimen storage vessel such as a storage vessel according to the invention.

24 Claims, 2 Drawing Sheets

Fig. 7

STORAGE VESSEL AND A BREAK TOOL FOR DIVIDING SUCH VESSEL

CROSS-REFERENCE TO RELATED APPLICATIONS

This application is the U.S. national stage filing under 35 U.S.C. §371 of international application PCT/DK2008/050338, filed Dec. 30, 2008, which claims benefit of Danish Patent Application 200800021, filed Jan. 7, 2008, each of which is incorporated by reference.

FIELD OF INVENTION

The present invention relates to a breakable multi-specimen storage vessel, comprising a tubular container comprising a lower end and an upper end, at least one end having an open end, the length of said container being continuously formed and provided with break portions at predetermined positions alongside thereof, where said container is adapted to be broken into to a plurality of specimens upon application of a radially directed force, an external surface of said container being provided with a screw thread.

The present invention further relates to a break tool for breaking off specimens from a multi-specimen storage vessel such as a storage vessel according to the invention, said break tool comprising at least a lower part comprising a tubular holder adapted for housing at least part of a lower end or an upper end of said storage vessel.

BACKGROUND OF INVENTION

Biological samples, such as substances in solution, e.g. blood samples, water tests, and tissue samples such as fertilized embryos, can often be effectively stabilized by freezing. The frozen fluid and/or sample will remain stable for extended periods of time as long as it is kept in the frozen state. Frequently these samples are collected in relatively large quantities, or collective sample, but could be utilized in smaller quantities, or specimens e.g. for test purposes.

When a specimen is needed, it often requires thawing of the entire collective sample to obtain the specimen currently needed, and then refreezing the remainder of the collective sample. However, frequent freezing and thawing cycles are almost always detrimental to the often unstable ingredients in the collective sample.

One solution is to store the collective sample in multiple small individual vessels. Then, when a specimen is needed, the necessary number of individual vessels may be thawed to provide the specimen needed without thawing and refreezing other individual samples of the collective sample. However, separation and freezing in individual vessels is cumbersome and time consuming, requires a larger amount of individual vessels, and thus larger storage facilities. The chance of confusion and mix-up of the individual vessels is also present.

WO 2004/042341 discloses a cryo preservation device and method for providing a collective vessel with individual, partial samples in the same cryo tube, separated by a gas-filled free space. This method and device provides excellently separated, well defined specimens, but requires investments in complex filling machinery using specified pressures, adjusted to the type and viscosity of the sample fluid.

U.S. Pat. No. 6,383,453 discloses a multi-aliquot storage vessel and corresponding break tool, where the vessel is provided with a number of equally distanced breakpoints, comprising of ring-shaped "notches" that extend around the perimeter of the vessel, and corresponding interior double ring-formed protrusions. One embodiment comprises external screw threads for closure caps, which threads are provided until a distance above and below said breakpoints. The break tool comprises an upper and a lower cylindrical part for housing each end of the vessel to be broken, which parts are provided with lips for abutment against the non-threaded parts of the vessel during breakage. The disclosed vessel may be difficult to manufacture in e.g. plastic or glass materials due to the provision of the internal protrusions. The disclosed break tool, when breaking a vessel as disclosed, must be positioned very carefully to avoid holding on to the treads in order to provide a clean break at the break points provided. This may prove difficult, when the second part is applied to the vessel too.

Accordingly, there is a need for a breakable storage vessel and break tool for breaking such vessel, which alleviate the above problems of the known vessels and tools.

SUMMARY OF INVENTION

In accordance with the present invention, there is provided a breakable multi-specimen storage vessel, comprising a tubular container, comprising a lower end and an upper end, at least one end having an open end, the length of said container being continuously formed and provided with break portions at predetermined positions alongside thereof, where said container is adapted to be broken into to a plurality of specimens, an external surface of said container being provided with a helical groove, wherein said helical groove is provided extending longitudinally along substantially the entire length of said tubular container and wherein an said internal surface of said tubular container is substantially smooth.

In a preferred embodiment, the container has a circular cross section, however, the container may have another shape, such as an elliptical, triangular, square, hexagonal, or other polygonal cross section or a cross section formed by combinations of the mentioned forms.

In a preferred embodiment, the container is adapted to be broken into to a plurality of specimens by application of a radially directed force, however other breaking means may also be used, such as breaking by twisting, bending or combinations of the mentioned breaking means.

By the provision of a substantially smooth inner surface, both in a longitudinal direction and going round the inside, where smooth is defined as the inner surface of the container being provided without recesses and/or projecting parts outside production tolerances, which may be from a few hundredth to a few thousandth of the wall thickness, the container in general does not require any further processing other than being moulded and/or blown. Thus, the production process is eased and the production costs are reduced. By reducing the production costs of each individual vessel it may indeed also enable cost effective mass production thereof. The container is made of any suitable method, such as moulding or extrusion. Further, the container is easy to empty, clean, and dry during use. In general, the container is provided as a disposable device, but one or more parts thereof may be suitable for reuse, depending on application. It has by the invention been realized, that any size, length and diameter, and section shape, such as circular, triangular, square, hexagon or other polygon, may be broken off when provided as a container vessel according to the invention.

Further, due to the provision of a helical groove covering substantially the entire outer surface of the tubular container, this enables the provision of break portions mutually distanced with a shorter distance than the storage vessels according to the known art. Accordingly, a frozen collective sample may be divided into smaller quantities or specimens without the need of thawing the entire collective sample and/or a larger selection of ranges of sample volumes of the specimens may be acquired. This increases the freedom of a user when deciding where to break off any needed volume of sample fluid. The helical groove may be continuous or discontinuous along the length of the container. It is however preferred that it is continuous. In a preferred embodiment, the helical groove is formed as a screw thread. By providing the helical groove as a screw thread it enables a tight seal of an applied cap having corresponding screw threads.

The container includes the possibility of one or more, e.g. multiple break portions at which the container can be divided along with its contents into one or more specimens, comprising one or more break portions. The remaining samples can be stored or transported for processing or testing without having to be thawed and refrozen.

In an embodiment of the storage vessel, said break portions are provided as a one or more ring-shaped external recesses extending around the perimeter of said tubular container. Thus, the break portions are easy to produce, e.g. by moulding, milling, etching or cutting, easy to break cleanly into specimens, and easy to place in relation to a break operation.

In an embodiment of the storage vessel, the depth of said recesses range between from 5 to 95%, preferably from 50 to 95%, more preferably from 90 to 95% of the total wall thickness of said tubular container. Thus, container integrity is maintained during handling and storing, while the break operation is facilitated.

In a preferred embodiment of the invention, at least one of the recesses is made by moulding. Thus, no further processing is needed during production, which reduces the production costs. In an embodiment of the storage vessel, at least one of said recesses is made by milling and/or etching. This eases the break operation, and reduces production costs compared to moulding of the recesses. In particular for glass containers this method of production is advantageous. In another, at least one of said recesses is made by cutting. This is advantageous when producing a soft plastic container.

In an embodiment of the storage vessel, two or more of said external recesses are provided equally distanced with a distance D, which distance range from between 1 to 100%, preferably from between 10 to 50%, more preferably from 33 to 40% of the entire length of the container. Thus, different size specimens may be broken off. It may be an advantage to place the recesses farther apart for providing a large volume of sample. However, it may on the other hand be more suitable to provide the recesses close together, e.g. 1-5 mm in between, to provide a wider selection of volumes to be broken off from the collective sample. Alternatively, the individual recesses are positioned sequentially, but not with an equal distance apart, e.g. for special applications using an increasing distance, e.g. doubling the distance.

In an embodiment of the storage vessel, said break portions are provided by said longitudinally extending screw thread being provided with a deep thread entering into at least a depth ranging from 5 to 95%, preferably from 50 to 90%, more preferably from 75 to 85% of the total wall thickness of said tubular container. Thus, freely selectable break portions are provided, which enables a large number of different size specimens to be broken off. The depth should match the depth of the screw threads upon applied caps.

In an embodiment of the storage vessel, it further comprises at least one screw cap provided with a screw cap thread which engages with screw threads provided upon the tubular container. Thus, a liquid and air-tight seal may be provided there between, which cap may be applied to either of the open ends of a broken off specimen, because the container screw thread is extending along the entire length of the container, and thus may use the same type of cap at each end.

In another embodiment of the storage vessel, it furthermore comprises at least one cap which engages with the container by a closing mechanism, such as sealing by snap caps, plugs, corks, screw caps, and at least one cap may have a cross section corresponding to the cross section of the container, such as a circular, elliptical, triangular, square, hexagonal, or other polygonal cross section.

In an embodiment of the storage vessel, the break portion is constructed such that when the storage vessel is broken, the resulting break is located only at the break portion area, whereby the ends of the separated specimens are rugged or fractured only at the break portion area, and whereby the screw thread will remain non fractured which allows the screw cap to fit smoothly on either of the broken off specimen.

In an embodiment of the storage vessel, said at least one screw cap is provided with an internal curving bottom. This provide easy access e.g. to a syringe needle in the bottom thereof, as the inner surface of such cap thus provides the bottom of the specimen broken off.

In an embodiment of the storage vessel, the material of the cap is softer than the material of the container. In another, the material of the cap is harder than the material of the container. Harder or softer is defined as the hardness during breakage temperatures, such as cryogenic temperatures, wherein cryogenic temperatures is used in its conventional meaning, i.e. below −80 degrees C., such as below −150 degrees C. This enables an easier attachment and detachment of the cap to/from the container. Alternatively, the two materials have the same hardness, and may also even be the same material.

In an embodiment of the storage vessel, the tubular container material is a plastic material. Said plastic material may be selected from the group consisting of polyethylene and polypropylene. In another embodiment, the material of the tubular container is a glass material. These materials resist and conform well to cryo temperatures, resist chemical agents well, provide easy production thereof, and are non-toxic to the samples. Further, these materials provide a vessel, which is easy to break during freezing temperatures. Said storage vessel may be a cryogenic storage vessel, but need not be, for example when the vessel is used for storing a fluid, which is fluid at room temperature, but solid a temperatures around 5 degrees C., such as stock for sauces, or when the fluid is crystalline at −3 degrees C., but fluid above, such as water.

In general the storage vessel may be used for any material which physical state can change from one state, e.g. a liquid state, into a solid state, depending on the ambient conditions, such as temperature and pressure. For instance, in one embodiment, the material is a gel having a phase transition from liquid to solid at a temperature greater than 0 degrees C.

In an embodiment of the storage vessel, selection of pitch depth and pitch width of the break portions and/or selection of material type and material thickness is determined accordingly for at the same time easing breakage and enabling secure storage and handling. Thus, according to application, different container diameters and/or lengths allow for different pitch depths and widths, and different material types and thicknesses, all selected relative to provide stable storage containers with eased breakage. The pitch shape may be any suitable shape, such as v-form or u-form.

In an embodiment of the storage vessel, at least the surface of said container is provided with identification markings for identifying at least the specimen taken, and/or identification markings for identifying at least the vessel, the specimen is taken from. In another embodiment said identification markings also marks the volume within. Thus, each individual specimen may be identified and traced to the mother collective sample/vessel. Further, each individual vessel may be identified, among several identical vessels. The volume is then precisely indicated and may be used for breaking off the desired length of specimen.

In a further aspect of the invention, there is provided a break tool suitable for breaking off specimens from a multi-specimen storage vessel such as a storage vessel according to the invention, said break tool comprising at least a lower tubular holder part adapted for housing at least part of a lower end or an upper end of said storage vessel, characterized in that at least said lower part is provided with a holding arrangement adapted for holding said storage vessel by limiting at least a longitudinal movement of said storage vessel within said lower part and for facilitating the breaking off of a user determined specimen of said storage vessel.

Thus, the holding arrangement within the break tool facilitates that the break tool holds the container or vessel during the break operation, and provides a more precise break point on the break portion provided on the container. By providing a holding arrangement, interruptions of the break operation will not lead to any need for rearrangement of the container within the tool. Further, the user determined length of specimen may easily be selected and arranged outside the lower part of the break tool for a more precise break surface on the resulting specimens. The break tool may further be suitable also for performing breakages on other types of storage vessels, such as conventional cryo tubes and the like. One example of a simple type of holding arrangement (not shown) is by providing a friction surface, such as a tightly fitting abutment surface or a friction increasing inner surface, such as a friction enhancing film or material cover. The length, section shape and inner diameter may of course preferably correlate to the vessel to be broken, but it has been realized, that the tool length is not decisive, as it has been realized with the invention that one may use an open-ended tubular holder part, or ring-shape, where one edge of this is providing the break off edge needed for breaking off the specimen needed.

In an embodiment of the break tool, a movement of the storage vessel with respect to the break tool is facilitated by a movement mechanism, so that, when one or more specimens is broken off, the storage vessel is moved in place for a new break operation.

In an embodiment of the break tool, it further comprises an upper tubular holder part adapted for housing either said lower end or said upper end of said storage vessel, at least part of an inner surface of said upper part adapted for providing an abutment surface for at least part of said storage vessel. This eases the break operation and provides less risk of damage to the container when broken and less risk of breaking at the wrong position. It may be that at least part of the inner surface of said lower part and/or upper part is adapted for providing an abutment surface for at least part of said storage vessel. Said abutment surface may be provided on at least part of said outer surface of said storage vessel. This provides a larger abutment surface, which reduces the risk of breaking at an incorrect position on the container. And/or said abutment surface may be provided on at least part of an outer surface of said cap upon said tubular container. Thus, the need for removing the cap before breakage is alleviated, which reduces the contamination risk of/from the sample within.

In an embodiment of the break tool, specimens, from a multi-specimen storage vessel, are broken off from both the lower end and the upper end of the storage vessel, such as one specimen from the lower end and two specimens from the upper end, without the use of a movement mechanism.

In an embodiment of the break tool, the break operation comprises twisting, bending, cracking, splitting and/or application of a radially directed force. When the break operation comprises twisting, the said holding arrangement preferably comprises a plier or other means which allow twisting.

In an embodiment of the break tool, said holding arrangement comprises at least said lower part being provided with a longitudinal throughgoing slit extending at least along a portion of said lower part, inside which slit is provided a transversal pin for limiting at least a longitudinal movement of said storage vessel within said break tool. Thus, the holding arrangement is realized by a simple construction, which makes the break tool easy to clean and low cost to produce. The holding arrangement, pin and slit, may be taken apart during cleaning and/or use, which increases the versatility and easy cleaning. Alternatively, they may be provided integrally with each other.

In an embodiment of the break tool, a length of said pin is extending transversally at least all the way through the inner diameter of said tubular holder part. Thus, only the longitudinal movement of the container is restricted in one direction (inward), allowing a realignment for a more appropriate break, and/or allowing a turning of the container within the tool, if that is needed, e.g. for determining volume or inspecting break portion position and/or sample content.

In an embodiment of the break tool, it is further provided with means for fixing said pin relative to the longitudinal direction of the tubular holder part. Said fixing means may comprise a throughgoing hole in the wall of the tubular holder part, the diameter of said hole being substantially equal to the diameter of said pin. Or said fixing means may comprise one or more grooves, provided opposite the throughgoing slit or the throughgoing hole. Thus, no relative movement of the pin inside the tool volume is possible, reducing the risk of a non-accurate positioning of the container therein.

In an embodiment of the break tool, two or more of said grooves were provided mutually distanced with a given distance L. L may correspond to D upon the container, but that is not required. L may be held constant between grooves or varied, according to needs and application.

In an embodiment of the break tool, said holding arrangement comprises an internally provided longitudinally extended matching screw thread for limiting at least a longitudinal movement of said storage vessel within said lower part and facilitating the selection of a user determined specimen of said storage vessel. This is advantageous when breaking a vessel according, for providing a freely selectable amount or volume of sample to be broken off. The holding arrangement is easy to produce and simple to clean. Both shown embodiments of the vessel may be used with such a break tool.

In an embodiment of the break tool, said lower part and/or said upper part is adapted for housing a vessel comprising one or more of said caps. Thus, the break tool can house the vessel even when one end still is provided with a cap. This reduces the risk of spillage and/or contamination of the sample within, because there is no need to remove the cap before breakage.

In an embodiment of the invention, a manchette, such as a sleeve, preferable made of a soft flexible material, for instance a disposable material, is arranged inside or outside the break tool and/or inside or outside the storage vessel for shielding the surroundings from spillage and/or contamination of the sample within the storage vessel when a specimen is broken off from the storage vessel.

In an embodiment of the break tool, the holding arrangement is arranged a distance from the breaking point to minimize spillage and/or contamination when a specimen is broken off from the storage vessel.

In an embodiment of the break tool, said lower part and/or said upper part is adapted as a cap of said storage vessel. Thus, a highly cost effective break tool is provided, in that the cap is adapted to become a break tool. Thus, both production and shipping costs may be reduced. The length of the cap may thus vary, according to application, and may, when applied fully to the container, cover one or more break portions. Thus, if a smaller sample is needed for break off, the cap is turned off, until it covers the appropriate length of container, after which that particular specimen is broken off.

In an embodiment of the break tool, it is provided with tool end parts on one end of said lower part and/or said upper part. Thus, if a break or spillage should occur during break operation, the risk of the user being contaminated is reduced. Further, the strength during use of the tool is increased, and the durability and holding resistance is increased.

In an embodiment of the break tool, a length of the open end of the upper and/or lower part is provided with a larger inner diameter than the remainder of the holding member. This improves the break point accuracy and inspection options of the user.

In another aspect of the invention, there is provided a system comprising a storage vessel according to the invention, and a break tool according to the invention. This provides the user with the utensils for providing specimens broken off with an increased break point accuracy.

DETAILED DESCRIPTION OF THE INVENTION

In the following the invention is described with reference to some embodiments shown in the accompanying schematic drawings, in which.

DETAILED DESCRIPTION OF THE DRAWINGS

Figure 1A:
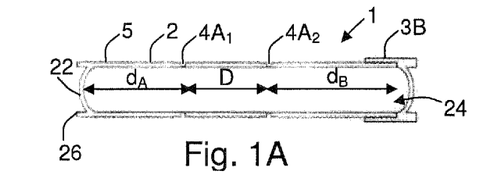
FIG. 1A, 1B shows a breakable multi-specimen storage vessel according to a first and a second embodiment of the invention.

FIG. 1A shows a breakable multi-specimen storage vessel 1 according to a first embodiment of the invention, suitable for containing a collective sample of e.g. a biological fluid sample and e.g. storing this at cryogenic temperatures. It is noted, that the vessel may be suitable for use in other applications, for example storing household or industrial cooking stock, as the vessel is used for storing a fluid, which is fluid at room temperature, but solid a temperatures around 5 degrees C., or for storing water bound samples, where the fluid is crystalline at −3 degrees C., but fluid above. Further, the samples kept within the vessel may be non-fluid and/or non-biological, as well, depending on application.

The storage vessel 1 comprises a cylindrical longitudinally extending tubular container 2 having a container bottom 22 at a closed lower proximal end thereof and an open end 24 provided with a securely fitting first end cap 3B at an upper distal end thereof.

The container 2 is provided with two externally provided ring-shaped break portions $4A_1$, $4A_2$ on a perimeter thereof, distanced mutually with a distance D, which break portions $4A_1$, $4A_2$ provides the possibility of breaking off three specimens in total from the vessel comprising the collective sample, a first specimen having a sample length of $d_A$, a second specimen having a sample length of D, and a third specimen having a sample length of $d_B$. The break portions are formed as ring-shaped cuts or recesses $4A_1$, $4A_2$ extending approximately half way through the thickness of the wall material of the cylindrical tubular container 2. The plurality of break portions $4A_1$ and $4A_2$ is formed along the length of the container 2 between the bottom end 22 and the open top end 24. The break portions $4A_1$, $4A_2$ separate the multi-specimen container 2 into individual specimens, which by breaking can be separated from the remainder of the collective sample as needed. The container wall interior opposite the break portions $4A_1$, $4A_2$ have a longitudinally plane, smooth surface in order to provide as large an interior volume as possible and for facilitating a low-cost production thereof. By the term smooth is meant that the surface is provided substantially without recesses and/or projecting parts outside production tolerances, such as less than a few hundredth to less than a few thousandth of the wall thickness. The break portions $4A_1$, $4A_2$ are designed to facilitate breakage of the container 12 at the break portion $4A_1$, since they constitute reduced wall thickness areas of the container 2.

Said recesses $4A_1$, $4A_2$ may be provided during production, e.g. by cutting, milling, moulding or the like. When choosing milling, applicant has observed a better willingness of the container material to break exactly at the point of the break portion. The depth of a recess is preferably selected relative to the hardness of the material of the container in such a way that both safe storage and handling, and an easy break operation is achieved. The depth of a recess may range between from 5 to 95%, preferably from 50 to 95%, more preferably from 90 to 95% of the total wall thickness of said tubular container 2, depending on container material selected. A remaining wall thickness of 5 to 10% is sufficient for maintaining container stability and securing handling. The shape of the recesses may be v-shape, u-shape, ]-shape or any other appropriate shape, and/or may differ or be of uniform shape along the container 2.

The distance $d_A$, D and $d_B$ may be selected appropriately during production relative to the intended use, specimen volume, and user needs. They may be of equal length, i.e. distanced with a distance D, which distance may range from between 1 to 100%, preferably from between 10 to 50%, more preferably from 33 to 40% of the entire length of the container 2. Said distance D may for in many uses correspond to 0.1-0.5 ml volume of sample within the container, depending of course on container diameter at hand, which in principle may be any diameter at hand, but in practice, in particular when applied to cryo tubes, often ranging from 1 mm to 50 mm in diameter. In general, often, it is useful and sufficient to provide the container with two break portions as shown; however, any number of break portions needed for any type of application is conceivable. Non-equally distanced break portions as shown in FIG. 1A are also conceivable, e.g. for special applications using increasing or decreasing amounts of volume for each test-sample.

The bottom 22 of the container 2 gently curves inwards to form a rounded bottom such as semicircular, convex, cone shaped or pyramidal, in order to provide space e.g. for housing a needle end. The container bottom wall 26 in the container bottom 22 is extending beyond the outer surface of the bottom 22 in order to provide stability, if placed on a plane surface and the bottom 22 extending downwards.

Further, said container 2 is provided with a screw thread 5 for matching and fitting a thread provided in each cap 3B. Substantially the entire length of the outer surface of the container 2 is provided with said screw thread 5.

Figure 1B:
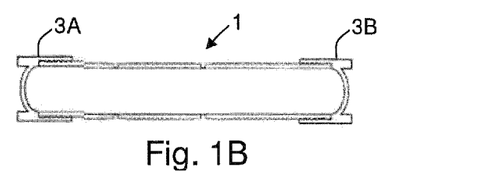

In an alternative embodiment shown in FIG. 1B the storage container may be provided with open ends 14A, 14B at both upper and lower end thereof. Preferably, a closing cap, a first cap 3A, and a second cap 3B is then provided at each end thereof in order to provide a secure fit thereto, reduce spillage, and provide stability standing on one end.

The storage vessel 1 may be broken into two or more specimens during use. The container 2 is designed such, so that a radially directed gentle manual or machine operated force will break the container 2 in two parts. Further, the container 2 is designed such that when the container 2 is divided in a manner that leaves both the lower part and the upper part with a new open end, see FIG. 2, one or two caps, 3C and 3D preferably similar to the one 3B provided for storage, can be attached to these open ends of the container 2. The third cap 3C is provided at the open upper end of said lower end 2A, and the fourth cap 3D is provided at the open lower end of said upper end 2B.

Figure 2:
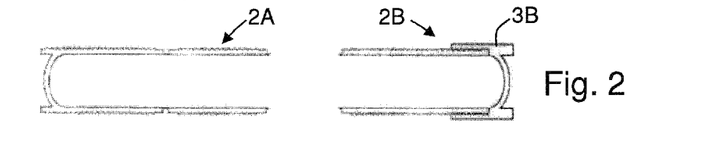
FIG. 2 shows the breakable multi-specimen storage vessel of FIG. 1A, after being broken into two specimens.

In FIG. 2 is shown a storage vessel of FIG. 1A, after it has been broken into two parts, a lower end 2A and an upper end 2B. There is not shown any biological sample within the storage vessel 2. However, it may advantageously be used for storing a fluid biological collective sample (not shown) filling out substantially the entire inside volume of the storage vessel 1. Further, the vessel 1 comprising collective sample may preferably be frozen, e.g. for cryogenic use, in order to provide a clean break surface of the two specimens of samples within upper 2A and lower end 2B, respectively of the storage vessel 1. When broken in a frozen condition, each broken off part will ideally contain frozen specimens, where the exposed surface thereof lies in a substantially flat planar perpendicular relationship to the outer wall surface of the container 2.

An outer surface of at least part of said container may further include information such as markings identifying at least the specimen taken, and/or identifying which vessel 1 said specimen has been taken from, e.g. a three to five digit (number, letter, symbol) code or codes in sequence extending peripherally and/or longitudinally along the longitudinal side thereof or the like. When being delivered in a collection of 100 to 1000 pieces of such storage vessels, the sequence of digits is preferably selected in such batch as not to result in any duplicate digit combination thereon. Thus, the risk of mix-up between specimens broken off and the remainder of the vessel before labelling thereof has been performed may be reduced, as it could happen in the case of dropping or misplacing one or more of said specimens.

Further, at least part of an outer container surface and/or outer cap surface may be provided with volume indication markings of the volume within, in sequence or using simple perimeter line markings, as is known to the skilled person. They may correspond to relatively small volumes, such as 0.1 ml each or larger volumes, such as from 0.1 ml up to 1 dl, depending on length and diameter of the container being used.

Said volume indication markings and said container and/or specimen ID markings may be provided in unison, or even as one and the same specific break marking.

Further, the vessel may be provided with further info, such as trademarks, producer name, and the like. The markings may include a planar longitudinally extending section for providing an adhesive ID label or barcode e.g. for individual specimen identification, date and/or user initials.

Said different types of markings may for example comprise written information, a number, barcode, and/or sign indication sequence, or any combination thereof, also stating production info, producer ID, and may be provided by labelling, moulding, etching, cutting or milling.

Figure 3:
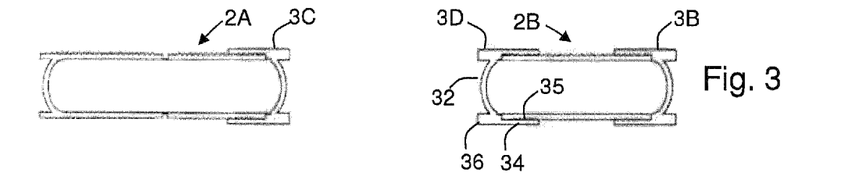
FIG. 3 shows the breakable multi-specimen storage vessel of FIG. 1A, being broken into two specimens; and being provided with securely fitting end caps.

FIG. 3 shows the two broken off ends or parts 2A, 2B being provided with each their similar matching closing caps 3C, and 3D, respectively. Thus, the upper part 2B of the container 2 comprising a first partial sample is available as a specimen e.g. for subsequent thawing and testing, and the lower part 2A comprising a second partial sample is available e.g. to be returned to the freezer for further storage, or vice versa.

The cap 3D, similar to the other caps 3A-3C includes a top surface on the bottom end 32, a side 34, and screw threads 35 provided on an internal surface of said side 34 for matching the corresponding screw treads 5 upon said vessel 1. The inner surface of the cap 3B is provided with a gentle curve or a convex shape in order to facilitate an eased insertion and use of a syringe needle into the bottom of it. The shape of the cap bottom may alternatively be otherwise rounded, pyramidal, cone shaped or simply flat. Further, the shape of the cap bottom also allows for said exposed surface to be protected, when said cap is applied to a specimen and/or remainder of collective sample after breaking off such specimen. Further, during application of a cap, the shape of the cap bottom 32 reduces the risk of contact and thus of chipping and/or transferring contamination off of the surface of the exposed part of the frozen sample from/to the cap bottom or sides. In a similar way, the bottom of the tubular container may be provided with any of the above mentioned shapes in order to facilitate syringe needle insertion or the like.

Figures 4, 5:
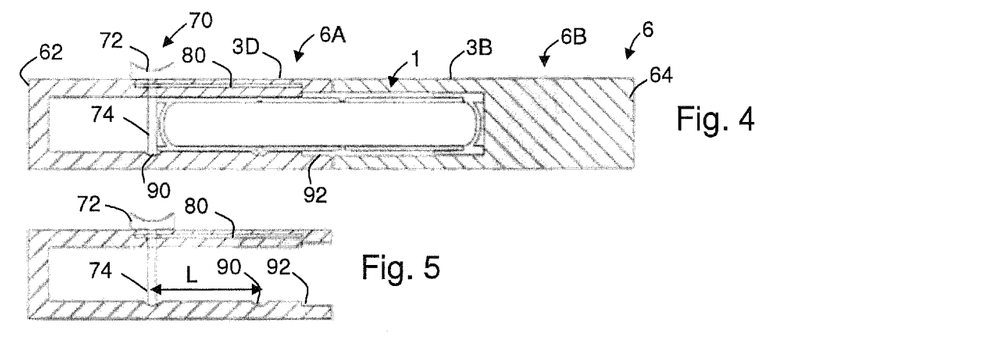
FIG. 4 shows a break tool according to a first embodiment of the invention, holding a storage vessel of FIG. 1A.
FIG. 5 shows a break tool according to a second embodiment of the invention, i.e. the break tool of FIG. 4 not comprising the upper part thereof.

Further, the cap form, i.e. diameter and design of sides fits snugly with the wall of the container in such a way that an easy screwing on of the cap is provided, and such that a secure tightening is allowed, for a secure fit of the cap to the container. As shown in FIG. 4, the sides of the cap do not extend further than before encountering a break portion recess, but it could do so, because it would not lead to a less tight fit with the container.

One or more of the caps 3A, 3B, 3C, 3D may preferably be supplied together with one or more of said containers 2.

By the invention, it has been realized, that by providing the container with an extensive all covering screw thread, the same type of cap having matching screw threads may be used for both ends of the container. Accordingly, a relatively low pitch of the thread is an advantage in order to match and provide a liquid tight seal against the container 2, depending on container diameter. However, in order to reduce the number of turns needed for applying the cap, a relatively high pitch is an advantage. A higher pitch may also be an advantage during production. Thus, a resulting pitch may be in the order of 1 mm to 3 mm. Appropriate heights of such pitch may be in the order of 0.3-0.5 mm, when the wall thickness is around 1 mm, i.e. a pitch height of around 30-50% of the wall thickness, and pitch widths may be selected of 0.5 to 1.5 mm, or may be chosen appropriately as known in the art, and any relevant technique may be used for providing such a seal and opening possibility, e.g. as are found with caps for bottles and the like.

The storage vessel 1, i.e. the tubular container 2 and one or more caps 3A, 3B, 3C, 3D should all be made of materials which can withstand deep freezing temperatures and which have got reduced resistance against radial breakage at least deep frozen. In general, a chemical resistant material is preferred, where some preferred materials include plastic materials such as polypropylene (PP), polyethylene (PEHD), polystyrene, or polycarbonate, but some glass materials resistive to temperature variances may also come into use. The caps and/or the container may further comprise rubber or plastic gaskets suitable for sealing during cryogenic temperatures.

The material used for the tubular container 2 may preferably chosen as to be easily mouldable and/or workable for providing break portions, such as cuts and/or threads therein, which are both durable during storage and handling, and easily breakable during dividing. The material may then preferably be chosen as polypropylene, because this material has increased brittleness during freezing temperatures.

Further, in order to provide excellent security against spillages, the cap 3, at least in room temperatures, may be of a more or less resilient and/or more or less hard material than the container 2, or vice versa. In the embodiment of the cap providing the break tool, the hardness of the cap, at least in freezing temperatures, may preferable by relatively hard, in order to provide a stable abutment surface for the container to be broken against. The material of the cap 3A, 3B, 3C, 3D may be softer than the material of the container 2 at room temperature and/or during breakage temperature, such as cryogenic temperatures, i.e. around minus 70 degrees C., or even higher temperatures, e.g. around zero degrees C., or higher yet. Further, the material of the cap 3A, 3B, 3C, 3D may be harder than the material of the container 2 at room temperature and/or during freezing temperature. That is to say that the hardness of the material of the cap and/or container may be chosen as to ease the application and detachment of the cap from the container, while at the same time provide a secure fit therebetween.

In order to increase readability of the volume or ID markings upon the container, the cap or caps may be provided in a transparent material.

The container may be produced by moulding, e.g. blow or injection moulding or the like, as is known to the skilled person, and different elements of the container, such as the threads, the markings, the recesses and/or the side extensions my be provided at the same time or machined after moulding.

The break portions 4A, 4B of the container may be specifically indicated, e.g. using peripheral colour line markings, metal or magnetic band marking, e.g. for use in further processing, or the like, for a further visual indication of the position of the break portion. A vessel 1 according to the invention is designed to be broken off into specimens using a manual break operation, but may also broken using a break tool, in which case, the risk of breakage in a wrong position or damage to the container is decreased. Examples of such possible break tools will be described below.

FIG. 4 shows a first embodiment of a break tool 6 according to the invention, comprising a lower part 6A and an upper part 6B for housing e.g. a storage vessel 1 according to the invention, as shown a vessel according to the first embodiment. The lower part 6A comprises a first tubular holding member adapted for housing and holding one end of the storage vessel 1, said first member being provided with a holding arrangement 70, 80, 90 for holding said one end of the storage vessel 1 and preventing said vessel 1 in sliding at least in one of the longitudinal directions.

The holding arrangement comprises a pin 70 or plunger having a length 74, inserted within a longitudinally extending, through-going slit 80 in the wall of the container. Said pin 70 is held in longitudinal position by the provision of a groove 90 opposite the entry point of the pin 70 into the slit 80. The pin 70 is provided with a handling bar 72 for moving said pin 70 between positions in opposite grooves 90. The slit 80 is extending at least along a portion of said lower part 6A and is preferably of a length that enables servicing one or more such grooves 90 by advancing the plunger sideways and stepwise for fitting into said grooves 90. The holding arrangement is provided for holding said container in place at least during the break operation by limiting at least a longitudinal movement of the container and/or vessel within said break tool 6. One or more grooves 90 may be provided as necessary for graduating the point of holding the container in place. The distance L between grooves 90 may be equally distanced or with different lengths, according to use and user desire.

Further (not shown), at least part of the length 74 of said pin 70 may be provided with a fixing thread for one or more corresponding fixing threads (not shown) within the inner surface of the slit 80, or it may be provided with a variable diameter/form (not shown) in order to fix the pin 70 within the slit 80.

One advantage of providing a pin 70, which is moveable within a slit 80 is that the pin 70 during use and after breakage of the required specimen may be handled by the user by operating the pin 70, after releasing the end thereof from the groove 90 and slide the pin sideways along the length of the slit 80 towards the container's open end, such that it moves and advances the specimen towards the outside of the open end of the break tool 6. Thus, a broken off specimen may be easily detachable from the break tool.

A length 92 of the open end of the upper and/or lower part 6A, 6B is provided with a larger inner diameter than the remainder of the holding member, in order to facilitate an accurate and clean break of the vessel 1, when the breaking force is applied thereto.

The diameter of the upper part 6A is substantially equal to the outer diameter of the vessel 1 that is to be broken, in order to provide an abutment surface between the outer surface of the vessel 1 and the inner surface of the holding member of the break tool 6, which abutment surface facilitates a safe break and provides a holding surface for said vessel 1 during application of a break force. Alternatively or in combination, the diameter of the upper part 6A may be adapted for housing said cap 3A, such that the outer surface of the side of the cap forms an abutment surface with the inner surface of the holding member of the break tool 6.

The lower part 6A is provided with a bottom end 62 for stabilizing the lower part, which provides a stronger tool, and reduces any risk of ending up with spilling broken of pieces of the container 2 and/or sample within, if the container 2 should break unevenly or even shatter.

The upper tool part 6B comprises a tubular holding member for providing an abutment surface between a vessel and the inner surface of the holding member. The advantage of the tool 6 being provided comprising an upper part 6B is, that the break force may be applied over the entire abutment surface of the vessel 1, which as shown in FIG. 4 is the outer surface of the side of the cap 3B, which often provides a lesser abutment area than when using a hand as upper part of the break tool. Thus, a more secure break may be performed utilizing the upper part 6A than without.

The lower part 6A is intended for keeping it immobile, e.g. against a surface such as the end of a table, and the upper part 6B is intended to be applied a radial force to, in order to break off along the break portion thereof. Preferably, the two parts are mutually identifiable in order to provide assurance of the position of the resulting break point.

The tool 6 may be provided as the lower part 6A, which works adequately without the upper part 6B, as shown in FIG. 5, which reduces the production and shipping costs of said tool. When using the tool, the users fingers on e one hand provides a firm hold against the outer surface of the vessel 1, and the other hand holds the tool 6A, while e.g. holding the tool against a flat surface, such as a table surface, or freely in the air, and applies the radial force needed to chip off the required specimen or specimens.

The material of the tool is not important to the function thereof, as long as it is durable enough to be useful during at least one break process. Suitable materials may be selected from any type of plastic, wood, glass, or the like, but may preferably be made of the same material as the cap and/or the container, in order to reduce an increase in production costs and provide an astatically pleasing visual presentation. Further, it may when applied to cryogenic temperatures be appropriate to make the tool from a material, which can endure and resist cryogenic temperatures, and even may become more durable in such temperatures.

The container may be produced in a plastic or glass material by moulding, e.g. blow or injection moulding or the like, as is known to the skilled person, and different elements of the container, such as the threads, the markings, the recesses and/or the side extensions my be provided at the same time or machined after moulding.

The outer surface of the break tool 6 may be provided with different markings (not shown) which may be useful e.g. for identifying the type (length, diameter, material, etc.) of container, said tool is adapted for, where said markings for example further may be written information, a number, barcode, and/or sign indication sequence, production info, producer ID, provided by moulding, etching, cutting or milling.

Figure 6:
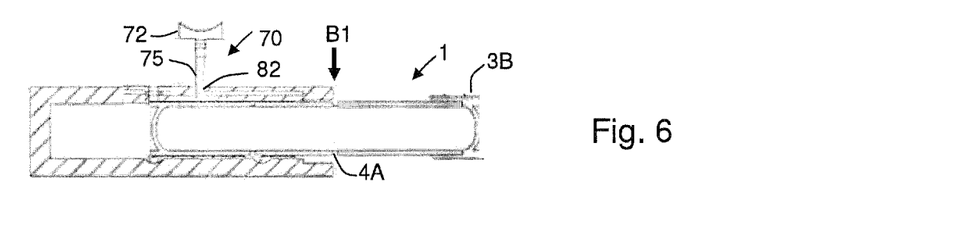
FIG. 6 shows a break tool according to a third embodiment of the invention, holding a storage vessel of FIG. 1A.

In FIG. 6 is shown a third embodiment of a break tool according to the present invention, comprising a lower holding member part, in which the holding arrangement comprises a pin 70 with a thread 75 for a matching screw thread inside the sides of a through-going hole 82 provided in the wall of the lower part. During use, when the pin 70 is turned using handle means 72 into the side of the lower part, the end of the pin is pressed into the outer surface of the storage container 2 or side of the cap 3A, which has been inserted to the position, in which the breakage will take part around the break portion 4A, which has been selected by the user for provide the needed volume of sample. Thus the holding arrangement keeps the container fixed, in the longitudinal and transversal direction, relative to the holding member at least during the break operation.

Figure 7:
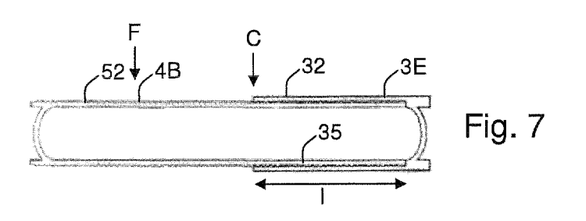
FIG. 7 shows a break tool according to a fourth embodiment of the invention, holding a storage vessel according to a second embodiment of the invention, wherein a cap forms the upper part of the break tool.

In FIG. 7 is shown a storage vessel 1 according to a second embodiment, comprising a plastic tubular container 2 provided with a longitudinally extending thread 52 provided along substantially the entire length of said tubular container 2. The depth of said thread 52 is increased, such that the thread itself constitutes the break portions 4B. Thus, said break portions are provided by said longitudinally extending screw thread being provided with a deep thread 4B. By the term "deep" is meant that the thread depth is entering into at least a depth ranging from 5 to 95%, preferably from 50 to 90%, more preferably from 75 to 85% of the total wall thickness of said tubular container 2. The profile of the deep thread may be selected appropriately, here a ]-profile may be advantageous both allowing easy breakage and providing a secure fit.

Thus, a completely individually selected amount of sample may be broken off, e.g. when handling individual specimens requiring very small volumes. The depth of the screw thread 52 matches the depth of the corresponding screw thread upon the corresponding cap in order to provide a liquid tight seal.

In FIG. 7 is further shown a break tool 6 according to a fourth embodiment, comprising a cap 3E, the side 32 of which is extended to a certain length l, e.g. from 100% of the total container length to 50% thereof, or any other useful length. The thread 35, which constitutes the holding arrangement and is provided in inner surface of the side of the cap 3E is extending along substantially the entire length thereof for engagement with the corresponding screw thread 52 provided in the outer surface of the container 2. Alternatively, the thread 35 may extend only partly from the upper end of the cap 3E, or only partly from the lower end, easing specimen detachment, or therebetween. The material of the cap 3E and/or the material of the container 2 are selected for safe storage and an eased breakage of the container into specimens. The cap side wall thickness may be further increased (not shown) in order to further stabilize and harden the break tool during use. Further, the shape of the cap may be cone or diamond shaped (not shown), the point of the cone or diamond pointing towards C, or any other shape providing a good grip and increased durability and eased breakage operation.

Thus the cap 3E itself upon the container 2 constitute an upper holding member part of the break tool. This cap break tool is in particular an advantage, if the collective sample is only intended to be broken off into two specimens. However, it is realized that breaking the container 2 off into several more specimens has been enabled in the following way: The cap may fit tightly to the container 2 during storage, as shown in FIG. 7. When a specimen is needed, the user releases the cap 3E, and turns it, until the needed volume (upper end) is reached by the end (C) of the side 32 of the cap 3E. Then the required specimen including cap 3E is broken off and thawed for use, while the remainder of the collective sample is left for further use, either provided with a new cap and stored again, or broken into smaller specimens using another break tool, either like the cap or like any other of the shown embodiments. Alternatively, or as a supplement, different length caps of this embodiment may be provided.

The container 2 or vessel shown in FIG. 7 may also be used in combination with any other type of break tool, also embodiments not shown, but obvious to the skilled person.

Thus, a holding arrangement is provided, comprising said matching thread 35, which holds the container 2 fixed relative to the holding member or cap at least during the break operation by limiting at least a longitudinal movement of said storage vessel within said lower part 6A and for facilitating the breaking off of a user determined specimen of said storage vessel.

During use, the cap 3B is applied, for example during a frozen state by turning the cap 3B until the required volume of sample as needed is reached by the lower end of the cap 3B (arrow C). Then the cap 3B and container 2 is held by the user in each hand and broken into two parts by using the necessary break force. Other alternatives are conceivable, for example the break tool is held fixed against a surface, such as a table or a wall, and the user breaks the specimen off using manually applied force, or the breaking off is performed automatically or manually using a force providing means, such as a motor operated winch, pawl or pin (not shown).

The vessel of FIG. 7 and the broken off specimens thereof may be used together with a cap 3A, 3C, 3D and/or in combination with a break tool according to any of the other embodiments shown.

Due to the low production costs, a system may advantageously be provided during production and/or delivery as a set. Said system can either be provided as a multitude of storage vessels and one or more break tools in a set, or be provided as one break tool for each storage vessel, i.e. as a combination. Thus, the diameters of the tool and container, respectively, may match accurately. Further, the provision of break portions upon the container may be aligned and perfectly matched to the holding arrangement of the break tool during production for providing the possibility of accurately breaking off the right number of break portions for a specimen holding the desired volume of sample.

EXAMPLES

A selection of 1-50 mm in diameter times 20-200 mm long cryo storage vessels in plastic, such as polypropylene and polyethylene with a wall thickness of approx. 1.0 mm according to the invention of FIG. 4 were produced and broken into specimens with a break tool as also shown. Some of the vessels were filled with water and some with plasma. The container was closed off with a cap as shown also in FIG. 4, and left for freezing at −80° C. for several hours. Initially, different depths of recesses were milled into a number of the containers, which were then tested by breaking off one or more specimens. The two recesses were positioned with a distance of xx apart. The result was that a remaining wall thickness of 5 to 10% is appropriate for maintaining container stability and securing handling, and provide easy breakage of the container at the recesses. It further was observed, that containers of a softer material, i.e. polyethylene facilitated breakage, i.e. was more brittle during breakage. Plasma containers provided a more planar sample surface of the resulting broken off specimens than did pure water.

In one test, the storage vessels were produced with a length of 81.2 mm, a diameter of 12.4 mm, a volume of 2.75 cm^3, and a weight of 2.14 g. The storage vessels may be produced in materials such as Borealis—Bormed HD810MO, LyondellBasell—Purell HM671T or Purell HP 371P.

The invention claimed is:

1. A breakable multi-specimen storage vessel, comprising a container, comprising a lower end and an upper end, at least one end having an open end, the length of said container being continuously formed and provided with break portions at predetermined positions alongside thereof, where said container is adapted to be broken into to a plurality of specimens, wherein said break portions are provided as one or more ring-shaped external recesses extending around the perimeter of said tubular container, and wherein the inner surface of the container is without recesses or projecting parts such that the internal surface of said tubular container is smooth.

2. The storage vessel according to claim 1, wherein the container has a circular cross section.

3. The storage vessel according to claim 1, wherein the container is adapted to be broken into to a plurality of specimens upon application of a radially directed force.

4. A storage vessel according to claim 1, wherein the external surface of said container is provided with a screw thread.

5. The storage vessel according to claim 1, the depth of said recesses ranging between from from 50 to 95% or from 90 to 95% of the total wall thickness of said tubular container.

6. The storage vessel according to claim 1, wherein at least one of said recesses are made by moulding, cutting, milling, or etching.

7. The storage vessel according to claim 1, wherein two or more of said external recesses are provided equally distanced with a distance D, which distance range from between 10 to 50%, or from 33 to 40% of the entire length of the container.

8. The storage vessel according to claim 4, wherein said break portions are provided by said screw thread being provided with a deep thread entering into at least a depth ranging from 50 to 90% of the total wall thickness of said tubular container.

9. The storage vessel according to claim 1, further comprising at least one cap which engages with the tubular container by a closing mechanism.

10. The storage vessel according to claim 9, wherein said at least one cap is provided with an internal curving bottom.

11. The storage vessel according to claim 9, wherein the material of the cap is softer than the material of the container.

12. The storage vessel according to claim 9, wherein the material of the cap is harder than the material of the container.

13. The storage vessel according to claim 1, wherein the tubular container material is a plastic material.

14. The storage vessel according to claim 13, wherein said plastic material is selected from the group consisting of polyethylene and polypropylene.

15. The storage vessel according to claim 1, wherein the material of the tubular container is a glass material.

16. The storage vessel according to claim 1, wherein the selection of pitch depth and pitch width of the break portions or the selection of material type and material thickness is selected accordingly for at the same time easing breakage and enabling secure storage and handling.

17. The storage vessel according to claim 1, wherein said storage vessel is a cryogenic storage vessel.

18. The storage vessel according to claim 1, wherein at least the surface of said container is provided with identification marks for identifying at least the specimen taken.

19. The storage vessel according to claim 1, wherein at least the surface of said container is provided with identification marks for specifying the volume within said container.

20. The storage vessel according to claim 1, wherein at least the surface of said container is provided with identification marks for identifying at least the vessel the specimen is taken from.

21. The storage vessel according to claim 4, wherein said screw thread is extending along the entire length of said tubular container.

22. The storage vessel according to claim 4, further comprising at least one cap which engages with the screw thread upon the tubular container.

23. The storage vessel according to claim 22, wherein said cap is provided with a thread which engages with the screw thread provided upon the tubular container.

24. The storage vessel according to claim 4, wherein said break portions are provided by said screw thread being provided with a deep thread entering into at least a depth ranging from 75 to 85% of the total wall thickness of said tubular container.

* * * * *